United States Patent
Krone (10) Patent No.: US 10,905,060 B2
(45) Date of Patent: *Feb. 2, 2021

(54) SEED PRODUCTION

(71) Applicant: Accelerated Ag Technologies, LLC, Urbandale, IA (US)

(72) Inventor: Todd Krone, Johnston, IA (US)

(73) Assignee: Accelerated Ag Technologies, LLC, Ankeny, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,485

(22) Filed: Jun. 24, 2016

(65) Prior Publication Data

US 2016/0374279 A1 Dec. 29, 2016
US 2018/0317412 A2 Nov. 8, 2018

Related U.S. Application Data

(60) Provisional application No. 62/269,514, filed on Dec. 18, 2015, provisional application No. 62/269,531, filed on Dec. 18, 2015, provisional application No. 62/269,496, filed on Dec. 18, 2015, provisional application No. 62/184,596, filed on Jun. 25, 2015.

(51) Int. Cl.
*A01H 1/02* (2006.01)
*A01H 6/46* (2018.01)
*A01H 6/54* (2018.01)

(52) U.S. Cl.
CPC ............ *A01H 1/02* (2013.01); *A01H 6/4684* (2018.05); *A01H 6/542* (2018.05)

(58) Field of Classification Search
None
See application file for complete search history.

(56) References Cited

U.S. PATENT DOCUMENTS

| | | | |
|---|---|---|---|
| 4,087,937 A | 5/1978 | Meador | |
| 5,596,838 A | 1/1997 | Greaves et al. | |
| 5,689,914 A | 11/1997 | Greaves et al. | |
| 5,694,700 A | 12/1997 | Greaves et al. | |
| 6,141,904 A * | 11/2000 | Greaves | A01H 1/02 47/1.41 |
| 6,146,884 A | 11/2000 | Coonrod et al. | |
| 6,865,556 B2 | 3/2005 | Penner et al. | |
| 8,158,850 B2 | 4/2012 | Feng et al. | |
| 8,356,464 B2 | 1/2013 | Lafargue et al. | |
| 8,618,358 B2 * | 12/2013 | Feng | C12N 15/8275 800/300 |
| 8,943,745 B2 | 2/2015 | Sexton et al. | |
| 9,227,230 B2 * | 1/2016 | Bensley-Bromilow | A01H 1/04 |
| 9,433,161 B2 | 9/2016 | Cope et al. | |
| 2013/0118066 A1 | 5/2013 | Cope et al. | |
| 2013/0118067 A1 | 5/2013 | Cope et al. | |
| 2013/0167496 A1 | 7/2013 | Bensley-Bromilow et al. | |
| 2014/0115730 A1 | 4/2014 | Cope | |
| 2014/0223812 A1 | 8/2014 | Cope et al. | |

FOREIGN PATENT DOCUMENTS

| | | |
|---|---|---|
| CA | 966734 | 4/1975 |
| CN | 104145947 | 11/2014 |
| CN | 104957032 | 10/2015 |
| CN | 205926293 | 2/2017 |
| JP | H11192033 | 7/1999 |
| JP | 2009040703 | 2/2009 |
| SU | 106770 A | 12/1975 |
| SU | 1061770 | 12/1983 |
| SU | 1606037 | 11/1990 |
| WO | 2012125593 | 9/2012 |

(Continued)

OTHER PUBLICATIONS

Wang et al. Industrial Crops and Products (2009); 29:182-188.*
Gupta et al. Theoretical and Applied Genetics (2019),132:2463-2483.*
Koga, Y., et al, (1971), Studies on the longevity of pollen grains of rice, *Oriza sativa* L. 1. Morphological change of pollen grains after shedding. Cytologia 36: 104-110.
Mouradian, R.; Womersley, C.; Crowe, L.M.; Crowe, J.H. (1985). Degradation of functional integrity during long-term storage of a freeze-dried biological membrane, Cryobiology 22:119-127.
Nirmala, B., et al. (2009). Economics of hybrid rice seed production in India. p. 495-503. In: F. Xie and B. Hardy (eds) Accelerating Hybrid Rice Development. Intl Rice Research institute.
Pfahler, P. L.; Linskens, H. F. (1972). In vitro germination and pollen tube growth of maize (*Zea mays* 42:136-140. L.) pollen Theoretical and Applied Genetics.

(Continued)

*Primary Examiner* — Medina A Ibrahim
(74) *Attorney, Agent, or Firm* — Brick Gentry PC; Brian J. Laurenzo; Jessica L. Susie (57) ABSTRACT

This invention describes a new method to generate hybrid seed in any crop plant while also reducing contamination from out-crossings and self-pollination. In contrast to conventional seed production methods, the method of the invention is not dependent on the use of any form of male sterility in the female parent plants, nor the use of isolation distances from unrelated and undesirable plants of the same species, nor the use of male parent plants in proximity to the targeted females. The process involves the delivery of pollen of the male parent at will, as available either in a preserved pollen bank, or using real-time collection from male plants as they become available. Desired pollen is delivered to fertile females during the period when viable pollen from the females and locally proximal unrelated plants is not being released. The delivered male pollen is in such amounts and fortuitously timed that it preferentially pollinates the females and produces relatively pure hybrid seed at levels much higher than if one used current hybrid production practices and did not utilize male sterility practices or prescribed isolation distances. Such fortuitous timing may involve the intentional application of pollen to females a day or two prior to female parent pollen becoming viable, and/or several consecutive mornings prior to female parent pollen or other proximal plant pollen beginning to shed each day.

32 Claims, 2 Drawing Sheets

(56) References Cited

FOREIGN PATENT DOCUMENTS

| WO | WO2013/070846 | 5/2013 |
|----|---------------|--------|
| WO | WO2014147005 | 9/2014 |
| WO | 2014209903 | 12/2014 |
| WO | 2016085355 | 6/2016 |
| WO | 2018129302 | 7/2018 |

OTHER PUBLICATIONS

Platt-Aloia, K.A.; Lord, E.M.; de Mason, D.A.; Thompon, W.W. (1986), Freeze fracture observations on membranes of dry and hydrated pollen from Colomia, Phoenix and Zea. Planta 168:291-298.

Platt-Aloia, K.A.; Thomson, W.W. (1985). Freeze-fracture evidence of gel-phase lipid in membranes of senescing cowpea cotyledons. Planta 163:360-369.

Priestley, D.A.; De Kruijff, B. (1982). Phospholipid motional characteristics in a dry biological system. A 31P nuclear magnetic resonance study of hydrating Typha latifolia pollen. Plant Physiol. 70:1075-1078.

Priestley, D.A.; Werner, B.G.; Leopold, A.C.; McBride, M.B. (1985). Organic free radical levels in seeds and pollen: the effects of hydration and aging. Physiol. Plant. 64:88-94.

Senaratna, T.; McKersie, B.D.; Stinson, R.H. (1985). Simulation of dehydration injury to membranes from soybean axes by free radicals. Plant Physiol 77:472-474.

Song, Z.P., et al. (2001). A study of pollen viability and longevity in *Oryza rufipogon*, *O. sativa*, and their hybrids. p. 31-32. IRRI Pub. 26.2.

Southworth, D.; Branton, D. (1971). Freeze-etched pollen walls of Artemisia pycnocephala and Lolium humboldtii. J. Cell Sci. 9:193-207.

Notification of International Preliminary Report on Patentability and International Preliminary Report on Patentability from PCT/US2016/039339.

Notification of International Preliminary Report on Patentability and International Preliminary Report on Patentability from PCT/US2016/039355.

Dickinson, H.G.; Elleman, C.J. (1985). Structural changes in the pollen grain of *Brassica oleracea* during dehydration in the anther and development on the stigma as revealed by anhydrous fixation techniques. Micron Micros. Acta 16:255-270.

Elleman, C.J.; Dickinson, H.G. (1986). Pollen stigma interactions in *Brassica*. IV. Structural reorganisation in the pollen grains during hydration. J. Cell Sci, 80:141-157.

Ganeshan, S., et al. (2008). Cryopreservation of Pollen. Ch. 17, In: B.M. Reed (ed), Plant Crypreservaton: A Practical Guide. Springer.

Heslop-Harrison, J. (1979). An interpretation of the hydrodynamics of pollen. Amer. J. Bot. 66: 737-743.

Heslop-Harrison, J.; Heslop-Harrison, Y. (1985). Germination of stress tolerant Eucalyptus pollen. J. Cell Sci. 73:135-157.

Hoekstra, F.A., and J. Bruinsma. (1975). Respiration and vitality of binucleate and trinucleate pollen. Physiol. Plant. 34: 221-225.

Kaku, S.; Iwayainove, M.; Gusta, L.V. (1984). Relationship of nuclear magnetic resonance relaxation time to water content and cold hardiness in flower buds of evergreen azalea. Plant Cell Physiol. 25:75-882.

Khatum, S., and T.J. Flowers. (1995). The estimation of pollen viability in rice. J. Exp. Bot. 46:151-154.

King, J.R. (1965). The storage of pollen—particularly by the freeze drying method. Bull. Torrey Bot. Soc. 92: 270-287.

International Search Report and Written Opinion of the International Search Authority regarding PCT/US2016/039355 filed on Jun. 24, 2016.

R T Weiland: Cross-Pollination Effects on Maize (*Zea mays* L.) hybrid yields, CAN, J. Plant Sci, vol. 72, No. 1, Jan. 1, 1992, pp. 27-33.

Cherng-Liang Tsai Et Al: Effects of cross-pollination on dry matter accumulation, nutrient partitioning and grain yield of maize hybrids grown under different levels of N fertility, Journal of the Science of Food and Agriculture, vol. 57, No. 2, Jan. 1, 1991, pp. 163-174.

J M Shete et al: Study of Heterosis in Top Cross Derivatives of Maize (*Zea mays* L.), Agric. Sci. Digest, vol. 31, No. 1, Mar. 1, 2011, pp. 1-7.

Want R F et al: Leaf photosynthesis is enhanced in normal oil maize pollinated by high oil maize hybrids, Industrial Crops and Products, Elsevier, NL, vol. 29, No. 1, Jan. 1, 2009, pp. 182-188.

Uribelarrea et al: Enhanced kernel set promoted by synchronous pollination determines a tradeoff between kernel number and kernel weight in temperate maize hybrids, Field Crops Research, Elsevier, Amsterdam, NL, vol. 105, No. 3, Nov. 19, 2007, pp. 172-181.

Carcova Jorgelina et al: Synchronous pollination within and between ears improves kernel set in maize, Crop Science, vol. 40, No. 4, Jul. 2000, pp. 1056-1061.

International Search Report and Written Opinion of the International Searching Authority regarding PCT/US2016/039339 filed on Jun. 24, 2016.

Synchronous Pollination within and between Ears Improves Kernel Set in Maize, Crop Science, vol. 40, No. 4, Jul. 2000, pp. 1056-1061.

International Search Report and Written Opinion of the International Searching Authority from PCT/US2017/027381.

Urs Weingartner, Olivier Kaeser, Muhua Long, and Peter Stamp: Combining Cytoplasmic Male Sterility and Zenia Increases Grain Yield of Maize Hybrids, Crop Science, pp. 1848-1856 (2002).

Barnabas, B. and Rajki, E. (1976). Storage of Maize (*Zea mays* L.) Pollen at −196° C. in Liquid Nitrogen. Euphytica 25:747-752.

Barnabas, B. (1985). Fertility of deep-frozen maize (*Zea mays* L.) pollen. Ann. Bot. 45:861-864.

Barnabas B.and Rajki, E. (1981). Effect of water loss on germination ability of maize (*Zea mays* L.) pollen. Ann. Bot. 55:201-204.

Barnabas, B; Kovacs, G.; Abranyi, A.; and Pfahler, P. (1988). Effects of Pollen Storage by Drying and Deep-Freezing on the Expression of Different Agronomic Traits in Maize (*Zea mays* L.). Kluwer Academic Publishers, Dordrecht—Printed in the Netherlands. Euphytica 39(3):221-225.

Barnabas, B (1994). Preservation of Maize Pollen Biotechnology in Agriculture and Forestry, vol. 25 Maize (ed. by Y. P. S. Bajaj) Springer-Verlag Berlin Heidelberg.

Barnabas, B., and G. Kovacs. (1997). Storage of Pollen. Ch. 14, In: K.R. Shivanna and V. K. Sawhney (eds). Pollen Biotechnology for Crop Production and Improvement. Cambridge University Press.

Basra, a. (1999). Heterosis and Hybrid Seed Production in Agronomic Crops, 81-84.

Collins, T. C.; Lertmongkol, V.; Jones, J. P. (1973). Pollen Storage of Certain Agronomic Species in Liquid Air, Crop Science, 13:493-494.

Connor, Kristina and Towill, Leigh. (1993). Pollen-Handling Protocol and Hydration/Dehydration Characteristics of Pollen for Application to Long-Term Storage, KluwerAcademics Publisher 77-84.

Crevecoeur, M; Clegg, J.S.; Seitz, P.; Seitz, W.; Hazlewood, C.F. (1982). Cellular responses to extreme water loss: the water-replacement hypothesis. Cryobiology 19:306-316.

Crevecoeur, M.; Deltour, R.; Bronchart, R. (1982). Quantitative freeze-fracture study of plasmalemma and nuclear envelope of *Zea mays* root cells during early germination, J. Ultrastruct. Res. 80:1-11.

Das, S.; Singhal, G.S. (1985). Role of interfacial structured water in membrane: osmotic properties of L-α-Egg lecithin liposomes. J. Membr. Biol. 86:221-227.

Communication pursuant to Article 94(3) EPC regarding European Patent Application No. 16 739 302.4 dated Feb. 12, 2019 Covering Seed Production.

Communication pursuant to Article 94(3) EPC regarding European Patent Application No. 16 738 296.9 dated Feb. 18, 2019 Covering Grain Production.

Communication pursuant to Rules 161(1) and 162 EPC regarding European Patent Application No. 17 718 712.7 dated Feb. 12, 2019 Covering Pollen Field Conditioning and Preservation Method.

Office Action dated Feb. 9, 2018 from U.S. Appl. No. 15/192,519 Covering Grain Production.

(56) References Cited

OTHER PUBLICATIONS

Office Action dated Apr. 12, 2019 from U.S. Appl. No. 15/486,737 Covering Pollen Field Conditioning and Preservation Method.
Ishikawa, M. Kitashima, T., Hemachandra, P.V., Yamaguchi, E. and Toyomasu, T. (2005), Seed Sci. & Technol., 33, 7541-752 Constant relative humidity chgambers using phosphoric acid for controlled desiccation of small recalcitrant.
Office Action dated Jun. 19, 2018 from U.S. Appl. No. 15/192,519 Covering Grain Production.
Tsai et al, Journal of the Science of Food and Agriculture 57: 163-174, Effects of Cross-pollination on Dry Matter Accumulation, Nutrient Partitioning and Grain Yield of Maize Hybrids Grown under Different Levels of N Fertility.
Wang et al, 2009, Industrial Crops and Products 29: 182-188, Leaf Photosynthesis is enhanced in normal oil maize pollinated by high oil maize hybrids.
Graybosch et al, 1988, American Journal of Botany 75: 144-156, Male Sterility in soybean—An Overview.
Ortiz-Perez et al, 2007, Field Crops Research 101: 259-268, Insect-mediated cross-pollination in soybean.
Sanford, J.C. and R. E. Hanneman, Jr., The Common Potato Pollen Collector Modified for Bulk Pollen Collection, 1977, News and Reviews.
Bhargava, et al, 1991, An Efficient Potato Pollen Extractor for Bulk Pollen Collection.
Office Action dated Apr. 30, 2018 from U.S. Appl. No. 15/486,737 Covering Pollen Field Conditioning and Preservation Method.
Almeida et al (Brazilian Journal of Botany (2011), Conservacao e germinacao in vitro de polen de milho, vol. 34 (4), pp. 493-497.
Volk, Gayle (2011) Collecting Pollen for Genetic Resources Conservation. Ch. 25.
Connor, Kristina F. (1993) Pollen-Handling protocol and hydration/dehydration characteristics of pollen for application to long-term storage.
Preliminary Requirement published by Industrial Property Review (RPI) No. 2560, of Jan. 28, 2020 regarding Application No. BR112017028054-0 in Brazil.
Cross-pollination effects on maize (*Zea mays* L.) hybrid yields, R. T. Weiland, Biotechnology Laboratory, EniChem America, Inc., Received Mar. 8, 1991, pp. 27-33.
Effects of cross-pollination on dry matter accumulation, nutrient partitioning and grain yield of maize hybrids grown under different levels of N fertility, Cherng-Liang Tsai, Don M. Huber, Herman L. Warren, Charles Y Tsai, Published 1991.
Study of Heterosis in Top Cross Derivatives of Maize (*Zea lays* L.), Article ID; ARCC918, pp. 1-7. J. M. Shete, D. B. Patel, M.P. Patel, R. A. Gami and C. G. Patel.
Synchronous Pollination within and between ears improves kernel set in maize, Jorgelina Carcova, Martin Uribelarrea, Lucas Borras, Maria E. Otegui, and Mark E. Westgate, pp. 1056-1061.
Enhanced kernel set promoted by synchronous pollination determines a tradeoff between kernel number and kernel weight in temperate maize hybrids, Martin Uribelarrea, Jorgelina Carcova, Lucas Borras, Maria E. Otegui.
Leaf photosynthesis is enhanced in normal oil maize pollinated by high oil maize hybrids, R. F. Wang, D. G. An, Q. E. Xie, G. M. Jiang, K. J. Wang.
Expert Report on Patent Application No. 201802926 from National Institute of Industrial Property, Chile, dated Jan. 6, 2020.
Communication pursuant to Article 94(3) EPC regarding European Patent Application No. 16 739 302.4 dated Dec. 13, 2019, issued by European Patent Office.
Time of Day of Pollen Shedding of Some Hay Fever Plants, Melvin D. Jones, PhD., Stillwater, OK, pp. 247-258, The Journal of Allergy.
Preliminary Requirement published by Industrial Property Review, of Jan. 17, 2020 regarding Application No. BR112017028059-0, issued by Servico Publico Federal Ministerio da Economia in Brazil.
Communication to Article 94(3) EPC regarding Application No. 16 738 296.9 dated Jan. 17, 2020 issued by European Patent Office.
Swift, J.G.; Buttrose, M.S. (1972). Freeze-etch studies of protein bodies in wheat scutellum. J. Ultrastruct. Res. 40:378-390.
Virmani. S.S. and M. Llyas Ahmed. (2001). Environment-sensitive genic male sterility (EGMS) in crops. Adv. Agronomy 72: 139-195. DOI: 10.10161/S0065-2113(01)72013-5.
Walden, D. B. (1967). Male Gametophyte of *Zea mays* L. Crop Science 7:441-443.
Wang, Z; Ge, Y.; Scott, M and Spangenberg, G. (2004), Viability and longevity of pollen from transgenic and non-transgenic tall Fescue (Festuca arundinacea) (Poaceae) Plants. American Journal of Botany 91(4): 523-530.
Webb, M.A.; Arnott, H.J. (1982). Cell wall conformation in dry seeds in relation to the preservation of structural integrity during desiccation. Am. J. Bot. 69:1657-1668.
Pareddy et al. (1989). Production of normal, germinable and viable pollen from in vitro-cultrued maize tassels. Theor Appl. Genet. 77:621-626.
Aylor, Donald E. (2004). Survival of maize (*Zea mays*) pollen exposed in the atmosphere. Agricultural and Forest Meteorology 123 (2004) 125-133.
Buitink et al. (2000). The effects of moisture and temperature on the ageing kinetics of pollen: interpretation based on cytoplasmic mobility. Plant Cell and Environment (2000) 23, 967-974.
Everett, H.L, (? 1950s?) Studies on Corn Pollen. Thirteenth Hybrid Corn Industry Research Conference.
Kerhoas C. et al. (1987). A multidisciplinary approach to the study of the plasma membrane of *Zea mays* pollen during controlled dehydration. Plane 171: 1-10.
Nath, J. et al. (1975) Effect of Freezing and Freeze-Drying on the Viability and Storage of Lilium longiflorum L. and *Zea mays* L. Pollen. Cryobiology 12, 81-88.
Nepi, M. et al. (2001). Pollen hydration status at dispersal: cytophysiological features and strategies. Protoplasma (2001) 216: 171-180.

\* cited by examiner

FIG. 1

SEED PRODUCTION

CROSS REFERENCE TO RELATED APPLICATIONS

This application claims priority from U.S. Provisional Application Ser. No. 62/184,596 filed Jun. 25, 2015 and entitled SEED PRODUCTION and from U.S. Provisional Application Ser. No. 62/269,496 filed Dec. 18, 2015 and entitled SEED PRODUCTION and from U.S. Provisional Application Ser. No. 62/269,531 filed Dec. 18, 2015 and entitled GRAIN PRODUCTION and from U.S. Provisional Application Ser. No. 62/269,514 filed Dec. 18, 2015 and entitled GRAIN PRODUCTION. The contents of U.S. Provisional Application Ser. Nos. 62/184,596; 62/269,496; 62/269,531; and 62/269,514 are hereby incorporated in their entireties by reference.

FIELD OF THE INVENTION

This invention relates generally to novel, on-demand seed and/or hybrid seed production technology (hereafter referred to as "hybrid seed"). More specifically, this invention relates to hybrid seed production technology which is not dependent on active pollen shed, male sterility, and/or physical isolation.

BACKGROUND

Figure 1:
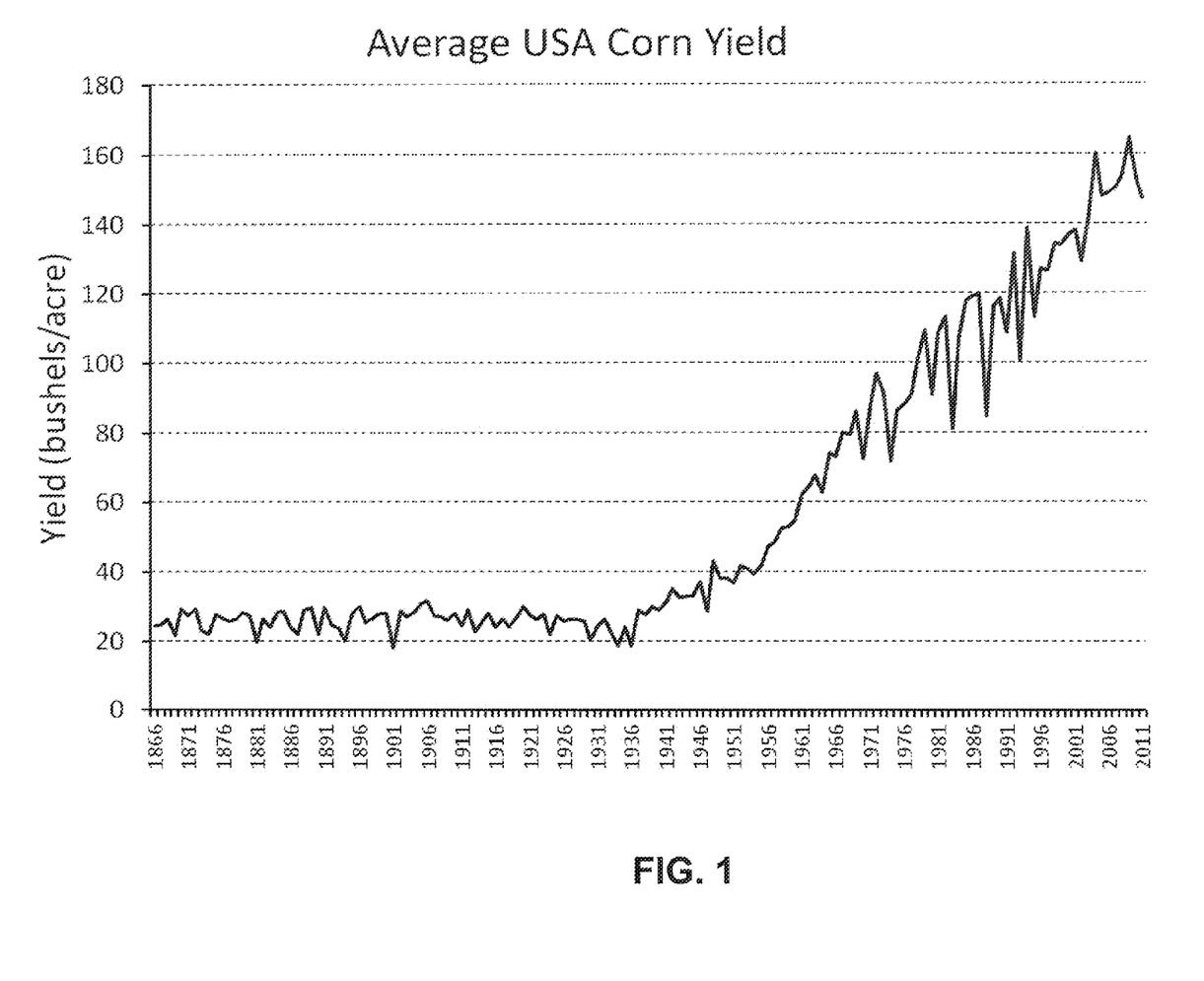
FIG. 1: This figure indicates the increasing average yield in bushels per acre of corn crops in the United States from 1866 to 2011. Source: University of Missouri Extension Website.

The current invention has application to the field of hybrid crop seed production and plant breeding practices, including, but not limited to, maize (also called corn), soybeans, wheat, rice, sunflower, canola, sorghum, cotton, barley, pearl millet, alfalfa, and other plants. Based on the location of the reproductive organ and the timing of fertility in plants, many species rely on self-pollination in order to produce fertile seed. Without implementing some form of mechanical, physical or genetic intervention to render a plant male sterile, many plants simply reproduce the genetics of their parent plant. Hybrid plants are the result of fertilization occurring from a male pollen source of one genetic background being crossed to the female reproductive organs of a plant with a different genetic background. Hybridity among crop plants generally gives a yield advantage in commercial production and is therefore preferred, if possible, to open or self-pollinated methods of producing a commercial crop. As shown in FIG. 1, crop yields began to increase markedly with the widespread introduction of hybrids in the 1940s, and crop yields have continued to increase steadily over time to the present day. Currently, maize, rice, sorghum, sunflower, and canola are the primary crops which take advantage of hybrid seed. The scale of hybrid seed production in other crops, such as soybean and wheat, is very limited due to the amount of resources required to overcome the obstacles presented by the biology of the reproductive organ structures and the unavailability of effective male sterility methods. Large scale processes to produce hybrid seeds from plant varieties which normally self-pollinate are lacking or inefficient, but would pose great value if made practical. It is widely known that planting and growing hybrid seed provides far greater seed yield potentials in comparison to planting and growing self-pollinated or varietal seed.

Soon after a new variety of hybrid seed is identified, farmers are generally eager to exploit the seed in their fields. Accordingly, seed production is required. Currently, most seeds are single cross hybrids rather than double cross hybrids, which were commonly used in the early 20th Century. However, either may be used. The shift to single cross hybrids was due to increased yield of such seeds. An enormous amount of land is required to produce all of the seed needed for farmers each season. In order to effectively produce the desired hybrid, pollinations must occur by the appropriate parents, which requires strict control over pollen sources. This often requires preventing the pollen of the designated female plant from pollinating itself, or self-pollinating. Typically, this is accomplished by inducing male sterility. In corn, for example, the female parents are usually de-tasselled. However, de-tasseling has drawbacks. First, it is expensive. Second, the plant is injured, which results in lower yields. To address the drawbacks of de-tasseling, other forms of male sterility have been proposed. Examples include cytoplasmic male sterility, genic male sterility, and chemically-induced male sterility. All have disadvantages.

Accordingly, for crops in which hybrid production is commonplace, current methods of producing hybrid seed vary by species, but typically involve the following components: (1) Planting female and male parent plants in a production block arranged in close proximity to one another; (2) locating the production block in an isolated location to reduce exposure to other unrelated or unwanted plants of the same species, and (3) imparting some form of male sterility to the female to render the female parent plants male sterile, thus avoiding the potential for self-pollination, which would ultimately contaminate the hybrid seed. The basic method of producing hybrid maize seed utilizing these three components has not changed since the first commercialization of hybrid maize in the late 1920s (Russell, W. A. (1974) Proceedings of the Annual Corn and Sorghum Industrial Research Conference 29:81-101). In hybrid seed production, the term "contamination" refers to seed that does not contain the desired and intended genetic cross between the female parent and male parent plants. Contamination can result from self-pollination by the female plant, or it can result from pollination of the female plant by pollen from an unintended male parent. This can be a result of pollen movement in the air or introduced via insects, wildlife, persons, vehicles, or other potential pollen carriers that enter the production field or are close enough to the female plants to inadvertently transfer pollen.

There are challenges to successfully implementing the isolation of production blocks, avoiding undesirable pollination events, and imparting male sterility. Procuring land which is isolated at a great enough distance from other plants of the same species is difficult and sometimes impossible to achieve. Therefore, it is not unusual for a field to be exposed to undesired pollen, thereby contaminating a certain percent of the seed produced in the field. Male sterility methods include genetic sterility, physical or mechanical removal of the male portion of the reproductive area on the plants which are intended for use as a female source, or a chemical gametocide that kills male gametes. Physical and mechanical methods are very expensive, while chemical gametocides are expensive and/or not very effective. Genetic male sterility in the form of cytoplasmic male sterility is used broadly in some crops like canola and sunflower, but is limiting in other crops such as maize and rice, in which the utility is limited because not all germplasm is compatible (Beckett, J. B. (1971) *Crop Sci.* 11: 724-727; Duvick, D. N. (1965) *Advances in Genetics* 13: 1-56). Nuclear genetic male sterility methods are mostly in development in the seed industry and only a few forms are commercialized, but are used in a small minority of hybrid production acres. While genetic male sterility methods are preferred to physical/ mechanical and chemical means, they still require significant resources to employ, they increase the complexity of creating trait stacks and getting products to market in the shortest timeframe, and sometimes must pass through complex global regulatory systems (for those requiring a GMO). Inherently, all of the methods of imparting male sterility in plants share the common denominator of incurring great expense and/or resources, as well as limiting products or product timelines, to complete properly.

Several economically important crops currently cannot be grown as hybrids (including, but not limited to, soybeans and wheat) because there is no efficient method of imparting male sterility and/or the species are so highly self-pollinating and pollen travels such short distances, that even with male sterility there would likely be poor cross-pollination success, resulting in a low yield of cross-pollinated hybrid seed, rendering hybrid production economically infeasible. In addition to soybeans, wheat is another valuable crop which to date has had limited success employing hybrid seed production. Generally speaking, the seed industry is actively pursuing methods to enable or improve hybrid crop production in most major crop species, driven by significant yield increases and breeding efficiencies that hybrid crop systems enable.

For crops that already utilize hybrid production (e.g. corn, sunflower), this invention totally or partially eliminates the need for, or reduces dependency upon, all three of the costly and resource dependent components previously mentioned: planting males in proximity to females, isolation, and male sterility. One widely-used method to create hybrid corn plants is to plant male and female parents in close proximity to one another, with each parent having the appropriate genetic makeup to create the preferred hybrid seed. As will be discussed in further detail below, each plant is capable of contributing both male and female gametes to produce seed. Accordingly, one parent line will be designated as having the appropriate properties for being used as a male source, while the other plants will be designated as the females. Male plants typically require good pollen shedding abilities, while the female plants must have adequate exposure of the female reproductive tissues as well as good seed yield and other desirable genetics. In widely practiced methods, the pollen shed from the male must overlap with the period in which the female plant is most fertile. Male plants typically occupy approximately 30% of the field with this number increasing to greater percentages in cases in which the male is a poor shedder of pollen, while the females occupy approximately 70% of the field. The males are present only to produce pollen for the designated female plants. Therefore, the land designated for the males has no productivity relative to seed or food production measures. The male plants also consume valuable resources, some of which include available minerals and moisture. Moreover, the plants which are designated as females must be sterilized with respect to their male characteristics in order to prevent self-pollination or pollination by the other designated females in the field.

As will be appreciated by one of skill in the art, the practice of the invention disclosed herein will provide different benefits depending upon the nature of the crop. For example, some crops have high rates of self-pollination due to pollen being released within the flower even prior to the flower opening. Such crops naturally experience very high rates of self-pollinated seed. Practice of the invention can reduce the percentage of self-pollinations, but due to self-pollination occurring prior to flower opening, the rate of successful cross-pollinations with designated male pollen will be lower than the rate in crops that do not have self-pollination occurring within the closed flower. Some crops do not require long isolation distances to prevent outcrossing due to the nature of the crop and its pollen characteristics. In such cases, the practice of the current invention may not affect any isolation requirement, but will still increase the rate of successful cross pollinations with designated male pollen and also decrease self-pollinations. Accordingly, depending upon the crop being grown, the practice of the invention may totally or partially eliminate the need for, or reduce dependency upon any one, any two or all three of the costly and resource dependent components previously mentioned: planting males in proximity to females, isolation, and male sterility.

Figure 2:
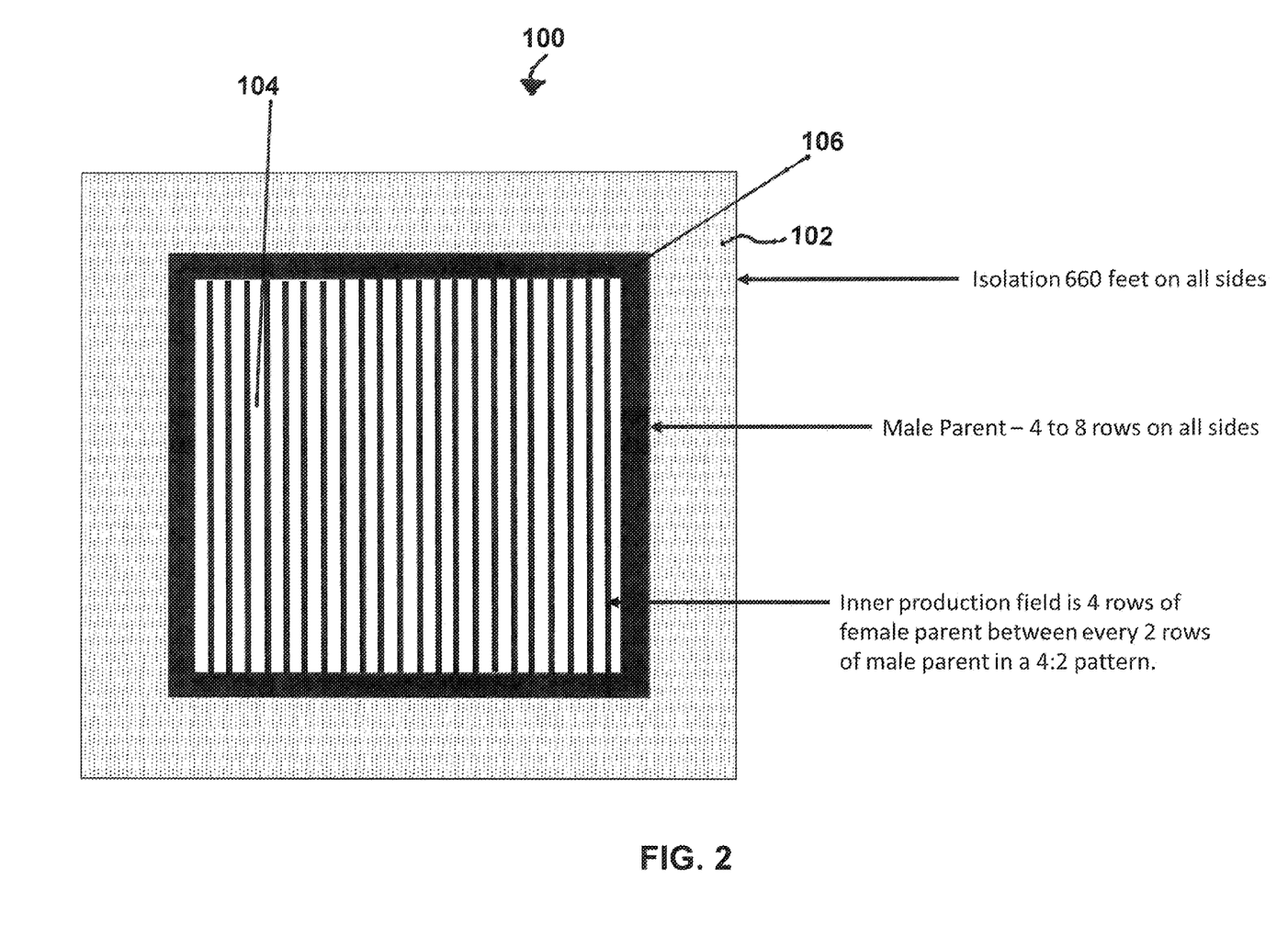
FIG. 2: This figure represents a top-down view of a typical maize hybrid seed production field. The outer light shaded square is the isolation border, typically planted with soybean. The inner black square represents male parent plants, and the inner field is an alternating row pattern of male and female parent plants.

In addition, it can often be difficult to find sufficient isolation from unrelated plants of the same species which have the potential to cause unwanted cross pollinations relative to the target cross pollinations. Facilitating this isolation can be expensive as well. For example, it is common in hybrid corn seed production to surround corn with other crops, such as soy, to achieve sufficient isolation. As shown in FIG. 2, a typical maize hybrid seed production field 100 is typically surrounded by approximately 201 meters (660 feet) of soybean crop 102 on all sides in order to achieve isolation. The soybean crop is depicted by the lightly shaded outer square in FIG. 2. The inner hybrid seed production field 104 has a border of 4 to 8 rows of male parent plants 106 on all sides as depicted by the black square in FIG. 2. The innermost portion of the hybrid seed production field is planted in rows of male parent plants alternating with female parent plants. In FIG. 2, this is shown in the common pattern of 2 rows of males between 4 rows of females. This pattern is not intended to be limiting—many patterns are used such that the male rows are interspersed between female rows at a common interval. Various planting patterns are used by growers depending upon the characteristics of the male and female parent plants and other factors that may be present at a given location. FIG. 2 results in a field that is approximately 35% male parent plants and 65% female parent plants. Based on a field of approximately 610 meters (2000 feet) in length with a width of 800 rows, the layout of FIG. 2 would result in approximately 37 hectares (92 acres) of seed production surrounded by 65 hectares (161 acres) of soy production acting as isolation. This requires a considerable amount of land area for a relatively small acreage of seed production. Other examples of hybrid seed production fields can use different combinations of male and female parent plants, and the decision of what pattern will be used is often dependent upon the characteristics of the parent plants.

To practice such a procedure on a production or commercial scale is both expensive and often insufficient to give the required genetic purity. Genetic purity is a measure of seed purity. In reference to hybrid seed, genetic purity is the measure of seeds that have the intended genetic cross between the male and female parent plants, and is typically expressed as a percentage. Seeds that result from self-pollination (selfs) or pollination with unintended pollen (out-crosses) are considered contaminants and are not hybrid seeds. Hybrid corn seed must typically have 95% genetic purity (i.e. 95% hybrid seed) to be sold as certified hybrid seed. Seed certification in the United States is a four-generation scheme that is the responsibility of each individual state, and within each state, there is an agency designated to certify seed based on the seed law of the individual state. The four generations are breeder seed, foundation seed, registered seed, and certified seed. Certified seed is produced from foundation or registered seed and is the final product of the four-generation seed certification program. Although each state has its own seed law, 95% genetic purity requirements are commonplace. Even when recommended isolation distances are used, it is common for undesirable pollen to contaminate the field due to pollen being carried by the wind, insects, and other factors of nature, from other fields within close proximity.

Among the methods to induce male sterility in the female parent plants in maize, de-tasseling is used for the majority of global seed production and is quite expensive due to the need for manual labor and/or expensive equipment to remove the tassels from the female plants. Since the wide adoption of corn hybrids in the 1930s (Crow, J. F. (1998) Genetics 148:923-928) seed production has mostly occurred in a very similar manner involving the planting of a seed production block of a male and female in isolation and de-tasseling of female rows. The invention described herein has economic value in that it can decrease the cost of goods sold (COGS) for the seed production process. First, the invention will save money on de-tasseling costs. The invention could allow for de-tasseling at an average of 50% of the intensity currently employed. Assuming a current de-tasseling cost of $350/A (Draft Environmental Assessment [online], 2010. Pioneer Hi-Bred international, Inc. Seed Production Technology (SPT) Process DP-32138-1 Corn [retrieved on 2016-06-19]. Retrieved from the Internet and approximately one million acres of hybrid seed production in the US alone (Weber et al., 2009. journal of Agronomy and Crop Science 193: 79-92), the current invention would have an annual value to the seed industry in decreased dc-tasseling costs of $175 million ($350/acre×50% adoption×1 million acres). In addition, additional value would be captured by decreasing isolation distances and decreasing amount of male that is planted in the seed production field. Genetic male sterility methods are less expensive than de-tasseling, but still carry substantial costs to the seed industry to develop the female lines with the correct genes/cytoplasm, to receive government regulatory approval to utilize the genes if they are considered GMOs, and to introduce products that are slightly delayed due to the development process timeline. For these reasons, genetic male sterility is used in a minority of the total maize hybrid units produced in the US. Similarly, chemical male sterility induction is used in a few crops and is considered expensive, relatively inefficient, and not broadly applicable.

Accordingly, there is a need in the industry for an invention which reduces the impact of, or entirely eliminates, the above drawbacks. Such an invention would reduce or completely eliminate the need to plant male parent plants in close proximity to female parent plants, or reduce the number of male parent plants needed. In addition, the invention would alleviate or significantly reduce the need to plant the seed production field in isolation from other unrelated plants of the same species through more controlled means of pollination procedures. Likewise, the invention would enable the use of shorter isolation distances. Moreover, the invention would reduce or eliminate the requirement of employing some form of male sterility in the designated female parents in order to avoid self-pollination, thereby greatly reducing or entirely eliminating the labor-intensive de-tasseling process or use of other male sterility methods.

In addition, for crops that cannot be grown as hybrids, or are difficult to hybridize due to morphological structure challenges or current breeding practices, the current invention could enable the production of hybrid seed and enable the production of commercial level quantities at a cost that would make hybrid production an economically feasible option for the seed industry. Efforts to hybridize wheat have been ongoing for over 80 years with little success in economically producing seed, despite the potential for yield gains from hybrid vigor in wheat of greater than 20% (Pickett, A. A. (1993) Adv. Plant Breed., Suppl. J. Plant Breed. 15: 1-259). A system that economically produces hybrid seed, such as the invention described herein, would have tremendous value. Assuming a modest yield increase of 10% for hybrid wheat compared to varietal wheat, and assuming that one third of the wheat acres would convert to hybrids, there would be an annual value of $4.3 billion globally for the entire value chain. This is based on 2014 global wheat production of 729MM metric tons (Food and Agriculture Organization of the United Nations (FAOSTAT)) and a wheat commodity price of $180.32 per metric ton (Jun. 13, 2016 wheat price, [online, retrieved on 2016-06-13] Retrieved from the internet (Calculation: $180.32/MT×729MM MT×10% yield increase×33% hybrid adoption). This total value is conservative, as claims by the seed industry are that the potential global value capture via the sale of seeds alone with approximately 33% adoption of hybrid wheat is approximately $3 billion annually (Syngenta Investor Day 2015 Presentation [online], page 20, [retrieved on 2016-06-19]. Retrieved from the Internet The number on a world wide scale is far greater yet.

SUMMARY OF THE INVENTION

Provided is a method of seed production wherein genetic purity of the resulting seed is improved by decreasing contamination comprising growing a designated female parent plant that includes both female and male components; intentionally pollinating, on one or more occasions, said designated female parent plant with designated male plant pollen when said male components of said designated female parent plant are not releasing viable pollen and when other biologically compatible pollen sources are also not releasing viable pollen; growing the designated female plant to maturity; and harvesting the seed produced by said designated female plant. Furthermore, the method includes the reduction or elimination of the need for one or more of the following conditions: male sterility of said designated female plant; physical and/or temporal isolation of said designated female plant from any biologically compatible pollen sources; and male pollinator plants to be grown in proximity of said designated female plant A further embodiment of the invention includes the use of either fresh or preserved designated male plant pollen. The pollen may have been harvested from one or more of a field, a growth chamber, a greenhouse, a glasshouse, a shade house, a hoop house, a vertical farming facility or a hydroponic facility. Preserved pollen may have been preserved by any means that permits the pollen to retain viability, including but not limited to various forms of cooling or freezing including, but not limited to, chilling, cryopreservation, freeze drying, or storage in liquid nitrogen. Furthermore the pollen, whether fresh or preserved, may have been collected from a source with altered circadian rhythm, a source with normal circadian flowering, but wherein said male components of said designated female patent plants are delayed, or a source with normal circadian flowering wherein the male components of the designated female parent plants are allowed to shed with no delay. The pollen, whether fresh or preserved, may have been collected from one or more genetic sources and may have been combined with pollen from other genetic sources before application.

In some embodiments, the male plant pollen is applied on more than one occasion to the same designated female plant. Embodiments of the invention include the application of the designated male plant pollen at the time which the designated female parent plant first becomes receptive to said pollen. Another embodiment includes the use of a treatment to delay the maturity of the male components of the female parent plant.

The method is applicable to a wide range of plants including, but not limited to, corn, soybean, wheat, rice, sunflower, canola, sorghum, cotton, barley, pearl millet and alfalfa.

Provided is a method of producing seed of any plant species, the method including the intentional application of designated male pollen to a designated female plant where the designated female plant parent is in a state when the female components are ready to receive pollen but the male components are not releasing pollen. Further, the designated female parent need not include male sterility and need not be isolated from undesirable biologically compatible pollen sources.

The application of the designated male pollen may be conducted by automated means, mechanical means, manual means, pneumatic means, positive pressure, negative pressure, semi-automated means, or combinations thereof. Moreover, the designated male pollen source may be from previously preserved or freshly harvested pollen from male source material.

DETAILED DESCRIPTION

The following is a detailed description of an embodiment of technology and methods enabling improved hybrid seed production. Such technology and methods may be used for the creation of hybrid seed from any plants. For ease of discussion and understanding, the following detailed description often refers to the invention for use with maize (also referred to as corn). It should be appreciated that the technology and methods may be used with any seed-propagated plants, and corn, or other specifically named plants are discussed for illustration purposes only and are not intended to be limiting. Similarly, the technology may also be used to decrease contamination and increase genetic purity in parent production and/or seed production in general. Contamination may be reduced by any amount, including but not limited to 5%, 10%, 15%, 20%, 25%, 30%, 35%, 40%, 45%, 50%, 55%, 60%, 65%, 70%, 75%, 80%, 85%, 90%, 95%, 100%, or any other amount. In preferred embodiments, contamination may be reduced by at least 30%, such as by 30% or more, 40% or more, or 50% or more.

Seed, including hybrid seed, is produced for a number of purposes. First, seed is produced for various research purposes to evaluate the value of new combinations of genetics. Seed companies devote billions of dollars to research in the pursuit of developing better plant genetics. Another reason to produce hybrid seed is for the commercial sale of such seed to producers, such as farmers. In addition, seed is produced to create the parent seed that is used to grow the parents in a hybrid seed production field. This invention can be used for the production of any hybrid or non-hybrid seed produced for any purpose. Regardless of the end use of the seed, the production of hybrid seed is dependent on the appropriate male pollen fertilizing the appropriate female. An improved method of hybrid seed production includes collecting, storing, and delivering pollen from male parent plants to the female parent plants. Some methods of collecting pollen are known in the art. For example, U.S. Pat. No. 4,922,651 discloses an apparatus for effecting or improving pollination of plants.

In addition, some methods of pollen delivery, such as U.S. Pat. No. 4,922,651, are known in the art. In addition, various methods of pollen storage are known. For example, U.S. Pat. No. 5,596,838, covering a method and instrument for the preparation of pollen for cryogenic storage, teaches that pollen can be stored for periods of months and still remain viable. Although some methods of pollen delivery are known, these methods do not teach, suggest, or motivate the user to intentionally deliver pollen in such a way that eliminates the need for isolation and/or male sterility that is always needed in the current art to support utilization in large scale field research or producing commercial hybrid seed. The current invention results in pollinations which occur outside the active period in which the plant might be subject to self-pollination and/or be exposed to other undesirable pollination, and thus does not require the use of male sterility or isolation, although one or both may be employed without departing from the scope of the invention. Moreover, in some plants, such as wheat, male pollen does not travel far enough to effectively produce hybrids (Loureiro, I. et at (2007) *Euphytica* 156: 25-37; Dong, S. et al. (2016) PLoS ONE 11(3): e0151373. doi:10.1371/journal. pone.0151373). The present invention remedies this problem in the industry by relying on intentional pollination in which the pollen is effectively delivered to the female parent plant.

As discussed above, the current invention is applicable to the common practice of planting female parent seed that will germinate and become seed bearing plants that will bear the hybrid seed to eventually be sold to farmers or other customers, or to producing seed for use in research programs. However, rather than planting the male parent seed in close proximity to the female plants as is the case with current practices, this invention provides an improved alternative through the use of intentionally applying male pollen to female plants at a specific time. Use of the term "intentional" with regard to pollen application means the specific application of pollen in a way that does not include natural pollination by wind, insect activity or other naturally-occurring conditions. Intentionally applied pollen is pollen that has been applied to a plant as a result of a deliberate human activity, decision, or intervention, and may be applied by hand or by other means. One example of intentional pollen application is the "prescriptive" application of pollen, which is the use of pollen to address a specific need or condition in the field. Although particular times are preferred, as will be discussed in detail below, one aspect of this invention is the advantage of pollinating in the field at any time of the day. In all aspects of the invention, the pollen may be obtained from one or multiple genetic sources.

The acquisition of male pollen [sometimes "pollen$^M$"] required to make the hybrid seed, can be via a pollen bank. A pollen bank is a source of stored pollen that has been collected from one or more pollen sources and stored in such a way that the pollen retains its viability. The plants that have been used as the pollen source for such a pollen bank may have been grown and harvested in any conditions, including but not limited to, a field, a growth chamber, a greenhouse, a glasshouse, a shade house, a hoop house, a vertical farming facility or a hydroponic facility. Pollen from a pollen bank may have been sourced in different ways. For example, in one embodiment, fresh pollen can be harvested from males grown in a controlled environment in which the circadian rhythm is 2-8 hours ahead of naturally growing female plants in the field. This method will be further detailed below. In another embodiment, the pollen which is stored in the bank may be preserved pollen that was collected days, weeks, months or years prior to its eventual removal from the bank for pollinating purposes. Preserved pollen may have been preserved by any means that permits the pollen to retain viability, including but not limited to various forms of cooling or freezing including, but not limited to, chilling, cryopreservation, freeze drying, or storage in liquid nitrogen.

In one or more embodiments, the pollen may be harvested from an anther studio. The anther studio enables optimal growth conditions for male plant reproductive tissues for any species or variety of plant. The tissues (corn tassels for example) are cut from plants growing in standard outdoor conditions, such as in the field or those grown in controlled conditions, such as the greenhouse or a growth chamber. The tissues are preferably cut prior to the plant beginning to shed pollen and are placed into the anther studio. The tissue may then be cultured in a nutrient medium allowing for further growth. At least one of specialized lighting, temperature, and/or humidity may be cycled in the anther studio, allowing for continued growth of the tissue. Growth may be modulated to increase or slow the rate of growth and thus modulate the duration for availability of pollen. This enables the ability to have on demand pollen for pollinations that can be accomplished at any time of the day or night. This has utility for pollination enablement of several beneficial and valuable processes related to seed and grain production. It also provides concentrated sources of pollen for preservation purposes. Any pollen harvested from the anther studio and preserved could be utilized in the same manner as the freshly harvested pollen, but at a duration long after the fresh pollen, which has not been preserved, has died. (R. I. Greyson (1994) Maize inflorescence culture. p. 712-714. In: M. Freeling, V. Walbot (eds), The Maize Handbook; Springer-Verlag, New York; J. B. Schoper, R. J. Lamber, B. L. Vasilas, and M. E. Westgate (1987) *Plant factors controlling seed set in maize. The influence of silk, pollen, and ear-learf water status and tassel heal treatment at pollination, Plant Phyiol.* 83: 121-125)

Delivery of the $pollen^M$, which may be by mechanical means, positive pressure, negative pressure, pneumatic, means, or otherwise, occurs as soon as females are receptive to pollen, which is always prior to the designated female parent's pollen [sometimes $pollen^F$] becoming viable on any given day, thus enabling a window of time during which successful cross pollination can occur with all receptive females. In other words, the female component of the plant is open to receive pollen from a male before the male component of the same plant is actually ready to produce pollen. In corn, females are receptive to pollen prior to emergence of the silks and for many days after emergence from the husks. Moreover, in corn, two possibilities exist: pollen may be shed prior to silk emergence (protandry) or silk emergence may be prior to pollen shed (protogyny). In either case, once the silks are receptive, they will be receptive to pollen before pollen is shed on a given day. This invention is applicable to both situations. Moreover, in some examples, the silks are receptive to pollen all day for about seven days. Accordingly, pollen may be intentionally applied any number of times, including but not limited to, once per day, twice per day, or in a continuous application. Without the use of male sterility, $pollen^F$ typically will begin to shed in the mid-morning hours, and continue to late morning or early afternoon, after which all $pollen^F$ either finds a viable female and germinates, enabling a successful self-pollination, or dies within 60 minutes or less if it does not land on a viable female (Luna V. et al. (2001) Crop Sci. 41(5): 1551-1557). Thus, the female corn plant has a daily window of time during which male pollen can be delivered and during which $pollen^F$ is not shedding. This window will be repeated over several days. Since the current invention cross pollinates nearly all of the viable females during a window of time during which $pollen^F$ is not shedding or is not viable, male sterility is not required to avoid self-pollinated seed.

Accordingly, one aspect of the invention is the timing of pollen delivery to female parents. In all crops, there is a daily cycle during the pollination window (the time during which the female is receptive to pollen and during which a successful pollination event can occur) in which females mature and grow relatively continuously, while males have a distinct cycle in which pollen becomes viable and sheds or is dehisced from the anthers beginning in mid-morning and ending in late morning or early afternoon. In some cases, $pollen^F$ can become viable prior to the females being fertile, but there will always be a first morning upon which viable females become fertile prior to viable $pollen^F$ beginning to shed on that day. Therefore, $pollen^F$ that may have shed the previous day has long since died and become inviable prior to females becoming viable the next morning. The early to mid-morning hours are therefore ideal for application of $pollen^M$ to fortuitously cross pollinate all viable females just prior to $pollen^F$ beginning to shed, although one may choose to apply pollen several days before $pollen^F$ beginning to shed or at several times of the day or in a continuous fashion to increase the probability of successfully creating pure hybrid seed. In one example, pollen may be delivered at 6:00 a.m. However, delivery of pollen may occur at any hour of the day, providing a great advantage over traditional methods. Thus, when $pollen^F$ begins to shed, all viable females have already been pollinated by the selected pollen source and the $pollen^F$ dies after a short period of time without finding any viable females, thus avoiding the self-pollination of females that has necessitated some form of male sterility in previous hybrid systems. Different species of pollen have different lifespans, which may be further affected by environmental conditions (Dafni, A. & D. Firmage (2000) *Plant Systemics and Evolution* 222(1): 113-132). Higher humidity and lower temperatures may extend pollen longevity. For example, in rice (*Oryza saliva*), pollen longevity has been found to be as short as 4 minutes (Koga et al. (1971) *Cytologia* 36: 104-110) or up to 20 minutes for 50% of the pollen to die (Khatum, S. and T. J. Flowers (1995) *J. Exp. Bot.* 46: 151-154). In contrast, field grown radish (*Raphanus sativas*) pollen was shown to have a 5-day lifespan (Siddiqui, B. A. (1983)*Acta Bot. Ind.* 11: 150-154).

Therefore, this invention takes advantage of the fact that once female receptivity to pollen is established, female components of plants are generally receptive to pollen before pollen is shed on a given day, even in cases where pollen is first shed overall prior to the female being receptive to pollen. In most, if not all plants, this occurs in a daily rhythm, such as with corn, in which female components are receptive to pollen and the male components are not ready until at least after the daily dew dries, which in some examples may be at 10:00 a.m. or as late as 1:00 p.m. on a cloudy or rainy day. Furthermore, on some poor weather or rainy days, the male components may be severely delayed or may never actually shed pollen. In many crops, such as soybean, the female components may be ready a day in advance of the male components. Often, the female is ready in advance of the male overall and on a daily basis. Accordingly, pollination first thing in the morning will often result in pollination by the desired pollen. Further, having the ability to pollinate at the very time in which the female first becomes receptive regardless of the time of day is a huge advantage over current practices.

By delivering pollen at the appropriate time and for the proper duration of a plant's fertility window, adequate purity can be achieved without the use of any form of male sterility in the female plants. This is the first time commercial hybrid seed production has been enabled in any crop without the use of some form of male sterility. Therefore, this is a novel aspect of the present invention. Further, since several crops, such as soybean, do not have a form of male sterility that is economically feasible, this invention enables hybrid seed production in species where it has either not been possible (e.g. soybeans) or has been difficult (e.g. wheat). In the same way, this invention enables for the first time effective hybrid seed production without the use of isolation, physical or temporal, from undesirable biologically compatible sources (pollen$^U$). Thus, when pollen$^U$ begins to shed, all viable target females have already been pollinated by the selected pollen source and the pollen$^U$ dies after a short period of time (1-4 hours) depending on species and environmental conditions, (Luna V. et al. (2001) Crop Sci. 41(5): 1551-1557; Stanley, R. G. & Linskens, H. F. (1974) *Pollen: Biology, Biochemistry, Management.* Springer-Verlag, Heidelberg; Shivanna, K. R. (2003) *Pollen Biology and Biotechnology.* Science Publishers, Inc.) without finding any viable target females, thus avoiding the cross contamination pollination of females that has necessitated some form of isolation in previous hybrid systems.

The capacity to deliver viable pollen on demand to effect timely pollinations of receptive silks addresses a number of limitations common to hybrid seed and grain production on a field scale. Specifically, prescriptive use of the invention overcomes low levels of pollen production, eliminates poor reproductive synchrony between male and female flowers, and decreases the high expense of physical isolation in hybrid seed production.

Embodiments of the invention include a range of options in addressing traditional isolation techniques. As discussed above, traditional isolation techniques may include physical isolation. The range of options addressing physical isolation may include the complete elimination of isolation from pollen$^U$, as well as a reduction in the isolation distances required to reduce pollen$^U$ contamination. A standard distance that is used for isolation in the US corn hybrid seed industry to isolate a hybrid seed production field, containing the male and female parent lines, from other corn is 201 metres (660 feet) or more (Iowa Seed Certification Requirements Handbook, Iowa Crop Improvement Association, 2009). While this distance can vary by state, the distance is typically significant in order to prevent pollen drift facilitated by wind, as well as insect-facilitated pollination. By utilizing the techniques of the invention disclosed herein, in combination with optionally reducing or eliminating the isolation distance of hybrid seed parents, a continuum of incremental genetic purity improvements can be made. For example, combining the pollination methods of the present invention with a reduction in isolation distances would result in an improved genetic purity level of the resulting hybrid seed. The isolation distance can be reduced from 201 metres to 180, 170, 160, 150, 140, 130, 120, 110, 100, 90, 80, 70, 60, 50, 40, 30, 20, 10, 5, or 1 metre of isolation distance, or the isolation distance can be eliminated entirely, such that the hybrid parent plant is planted directly next to other corn that is not the intended crossing parent. As the isolation distance is reduced, there is a higher potential for a lower purity level, but because of the efficacy of the pollination techniques disclosed herein, the purity levels achieved may still be within the required standard for the production and sale of hybrid seed. The traditional requirement for physical isolation from adventitious pollen sources adds a major expense to hybrid seed production. Direct application of pollen in accordance with the invention to receptive silks at doses sufficient to ensure high levels of fertilization prior to local pollen shed overcomes the need to practice seed field isolation.

In addition to physical isolation, temporal isolation is a technique which may be used to isolate females from pollen$^U$ contamination. Temporal isolation occurs when females and undesirable males are planted at different times, such that the female silks and pollen$^U$ are available at different times. In one, non-limiting example, the females and males may be planted a month apart. Such a technique is most often used in tropical and sub-tropical climates. Embodiments of the invention include a range of options in addressing temporal isolation as well. The range of options addressing temporal isolation may include the complete elimination of isolation from pollen$^U$, as well as a reduction in the isolation times or quantities required to reduce pollen$^U$ contamination. Because of the efficacy of the pollination techniques disclosed herein, the purity levels achieved may still be within the required standard for the production and sale of hybrid seed.

Close synchrony between male and female flower anthesis, and a minimum pollen density per exposed silk are fundamental requirements for high levels of seed production and genetic purity. Previously collected and preserved pollen, or fresh pollen, can be applied to receptive silks over a period of seven to ten days, ensuring seed set under conditions of decreased pollen viability, silking delay relative to pollen shed, or poor 'nick' between male and female inbreds. In the agronomic industry, "nick" is a term used in hybrid seed production that refers to the synchrony of both male and female flower types (i.e. the peak of pollen shed by the male aligned with the peak of silk emergence in the female) developing at the ideal time such that pollen grains will successfully pollinate, resulting in fertilization. For seed producers, the perfect "nick" occurs when 50% of the male population begins to shed pollen on the same day when 50% of the female population begins to exert silks.

A similar continuum of purity improvements applies if the pollination techniques of the present invention are utilized in tandem with a reduction in the amount of de-tasseling in a field. De-tasseling standard practices require that no more than 1% of the female tassels are allowed to shed pollen (Iowa Seed Certification Requirements Handbook, Iowa Crop Improvement Association, 2009). In order to accomplish this, a de-tasseling crew may need to pass through a field on 4-5 consecutive days and at various levels of intensity (speed at which de-tasselers move through the field on any given pass). By utilizing the techniques of the invention disclosed herein, de-tasseling passes and/or intensity can be decreased, allowing more than 1% of the female tassels to shed while still obtaining acceptable genetic purity. The percent allowed to shed can be increased from 1%, 2%, 3%, 4%, 5% to 10%, 20%, 30%, 40%, 50%, 60%, 70%, 80%, 90%, or 100%. In the case of 100%, no de-tasseling would be required.

A similar continuum of purity improvements applies if the pollination techniques of the present invention are utilized in tandem with a reduction in the number of male plants required to be planted in order to successfully pollinate a field of females to obtain the necessary level of genetic purity. In a typical maize hybrid seed production field, male parent plant presence ranges from 20% to 40% of the plants in the field (Basra, A. S. (1999) *Heterosis and Hybrid Seed Production in Agronomic Crops*, p. 48). The percentage of male parent plants required will depend upon a number of factors including the anticipated pollen vigor and viability that the pollen from the male parent plants will demonstrate, as well as factors related to the particular land area and climate. Practice of the present invention will allow for significant reduction in the percentage of male plants needed in a field, or allow for their elimination entirely. For example, instead of needing 40% male parent plants in a production setting, a smaller percentage could be used, such as 35%, 30%, 25%, 20%, 15%, 10%, 5% or even 0% male parent plants in the field. Prescriptive application of pollen in accordance with the invention has the potential to entirely eliminate the male pollinator from a seed field.

Moreover, a similar continuum of purity improvements can also be applied to crops wherein one or more plants may self-pollinate before the plant flowers and is able to receive other sources of pollen. One non-limiting example of such a crop is wheat. The present invention may be advantageous to such crops. For example, limited male sterility and/or isolation may be applied. Furthermore, females could be bred to flower early or subject to mechanical or physical disturbance to cause the flowers to open. Pollen may also be forced into a flower on some occasions. Even in cases where some self-pollination is inevitable from such an occurrence, proper hybrid pollination may occur in the plants where the flowers open prior to self-pollination. In such a case, genetic purity is improved.

Pollen grains are small and can be very delicate. Their ability to successfully pollinate a female can be compromised by a range of environmental stresses, and can also be inherent qualities passed on by the plant producing the pollen. Pollen performance (i.e. speed of germination, vigor of tube growth) can be referred to as pollen vigor, whereas the ability of pollen to successfully sire viable seeds may be referred to as pollen viability (Shivanna, K R et al. (1991) Theor. Appl. Genet. 81(1):38-42). Pollen vigor and viability can vary significantly among plant species, cultivars, and varieties. In some cases, it may be desirable to practice the invention using a pollen that typically has poor vigor and/or viability. In such circumstances, although the practice of the invention is expected to increase yield and improve purity, the percentage improvement in each of these characteristics may be low in comparison to using pollen with higher vigor or viability. Accordingly, there is a continuum of improvement for both purity and yield that may be achieved by the practice of the present invention that may be dependent upon a wide range of factors including pollen vigor and viability. In the event that purity improvements are small, additional steps may be taken to improve purity levels as described later in this disclosure.

As will be appreciated by one of skill in the art, the selection of the male pollen to be used in the practice of the invention is a significant factor in the potential benefit recognized by practicing the invention. Pollen vigor and viability are considerations, along with the various traits and characteristics that can be conferred by the pollen. There may be circumstances when using a pollen with lower vigor or viability is still a good choice because of the traits that it will confer upon the resulting seed. In such circumstances, when a pollen is known to have a lower vigor or viability, a more moderate resulting decrease in contamination should be expected, along with lower potential yield increases. Such decisions can be made by the grower based on the particular characteristics of the crop, the desired seed, and prevailing conditions at the anticipated time of pollination with regard to environment and other biotic and/or abiotic pressures affecting the crop. Accordingly, the ability to select the pollen at the time of pollination is a further significant factor in the potential benefit recognized by practicing the invention. Table 1, below, outlines selected potential benefits of using the invention.

TABLE 1

Example Benefits of Pollen Selection

| Production Problem | Application of the Invention | Expected Benefit |
| --- | --- | --- |
| Poor pollen production by male inbred, not suitable for hybrid seed production on a field scale | Use of fresh or preserved pollen applied to receptive silks on demand thereby increasing pollination | Greater potential to utilize elite male inbreds in hybrid development |
| Low level of seed production in parent seed fields | Use of fresh or preserved pollen applied to receptive silks on demand thereby increasing pollination | Greater seed production by elite male and female inbreds |
| Poor reproductive synchrony between male and female inbred in hybrid seed production leading to low seed yield and higher than acceptable level of genetic contamination | Use of fresh or preserved pollen applied to receptive silks on demand thereby increasing pollination | Increased seed yield per acres, decreased self pollination of female inbreds, decreased outcrossing from adventitious sources |
| High expense of hybrid seed production due to requirement for physical isolation from adventitious pollen sources | Use of fresh or preserved pollen applied to receptive silks on demand thereby increasing pollination | Direct application of pollen to receptive silks at doses sufficient to ensure up to 100% fertilization prior to local pollen shed overcomes need to practice seed field isolation |

TABLE 1-continued

Example Benefits of Pollen Selection

| Production Problem | Application of the Invention | Expected Benefit |
|---|---|---|
| Inbreeding effect of a monoculture field wherein pollination is by a plant of identical genetic make-up, such as by self-pollination or sibling pollination | Use of fresh or preserved pollen applied to receptive silks on demand thereby increasing pollination | Increased seed yield per acres, decreased self pollination of female inbreds, decreased outcrossing from adventitious sources |

The following non-limiting example provides a potential scenario in which the invention can be practiced, and outlines the benefits. The invention can be practiced in the case of a hybrid that consists of a poor shedding male that requires 35% or more male presence in a hybrid seed production field using conventional methods, and yet still results in borderline acceptable contamination (~5%). The invention could enable decreasing male presence in half to 17% presence, while also decreasing contamination to an acceptable level (2-3%), and decreasing the cost of goods sold. Alternatively, if the male is an above-average pollen shedder, and pollen was captured and preserved in previous parent increases, the invention could enable the elimination of males and decreasing de-tasseling intensity (and costs) by 50%, resulting in a decrease in the cost of goods sold, while maintaining contamination at levels equal to the conventional practice (2-3%), but at contamination levels dramatically lower than the same parameters (50% de-tasseling intensity, and no male presence) without practicing the invention.

Pollen$^M$ can be delivered in any number of ways, including, but not limited to, manual delivery, manual delivery with a small hand mechanical device for semi-automated dispersal, by field driven machinery containing pollen dispersal machinery or via fully automated dispersal by a self-propelled and/or human guided apparatus such as a drone that has a pollen dispersal device mounted to it, wherein the pollen dispersal is by automatic means, including, but not limited to, mechanical means, positive pressure, negative pressure, or pneumatic means. Use of a drone would be especially novel and practical in this method. Small drones, which need not be regulated, to be used in the method, and which can be guided using GPS coordinates to focus the pollen dispersal directly over the female plants. Using any of these methods, it has been estimated by the inventors that about 140 grams (5 ounces) of pollen$^M$ fortuitously delivered for 3-4 consecutive days is enough to successfully cross pollinate one hectare (2.47 acres) of corn female parent plants with adequate purity to meet current state seed laws in the US as previously described herein, which generally require less than or equal to 5% contamination (self-pollinated and outcross contaminant seed combined) in order for seed to be certified and sold commercially. This estimate is based on literature that provides the number of maize pollen grains per mg, and estimating approximately 3 to 5 grains or pollen per silk, or fewer, for successful pollination (3-4 grains of pollen per silk is commonly accepted by those skilled in the art of pollination as the amount needed to ensure successful pollination (M. E. Westgate, J. Lizaso, W., Batchelor (2003) *Quantitative relationships between pollen shed density and grain yield in maize, Crop Science* 43: 934-942; M. Uribelarrea, J. Carcova, M. E. Otegui, M. Westgate (2002) *Pollen production, pollination dynamics, and kernel set in maize, Crop Science* 42: 1910-1918).). See, for example, Porter (1981) *Environ. Health Perspectives* 37: 53-59; Miller (1982) In *Maize for Biological Research*. W. F. Sheridan (ed.), pp. 279-293). The timing of pollen delivery, amount of pollen required, and number of days of pollen delivery can be adjusted as necessary for circumstances that vary, such as variation in the amount of pollen various female parents produce and weather patterns (i.e. rain frequency or amount, wind speed and direction, etc.). For example, the method can be adjusted and customized for any given set of parents depending on the pollen producing capabilities of the male and female. Moreover, it is anticipated that the efficiency of these delivery methods will reduce the amount of pollen needed for hybrid pollination. It is estimated by the inventors that these more efficient methods may use, on average, 1/1000 or less of the amount of pollen currently produced for hybrid seed production. The inventors' research indicates that perfect corn kernel set requires about 3000 pollen grains per silk as shed normally in the field from maize tassels. Hand pollination studies and open field studies indicated about 3 to 4 pollen grains per silk ensure kernel set. (M. E. Westgate, J. Lizaso, W., Batchelor (2003) Quantitative relationships between pollen shed density and grain yield in maize, Crop Science 43: 934-942; M. Uribelarrea, J. Carcova, M. E. Otegui, M. Westgate (2002) Pollen production, pollination dynamics, and kernel set in maize, Crop Science 42: 1910-1918). This results in a ratio of about 1/1000$^{th}$ of the amount of pollen currently required for hybrid seed production.

Therefore, practice of this invention simultaneously eliminates the need for male parent plants being present in proximity to the female parent plants as well as the need for any form of male sterility to be present among the female parent plants. Moreover, one skilled in the art can easily vary from the examples listed above as necessary. For example, in some situations, it may be advantageous to pollinate at night. In others, it may be advantageous to pollinate all day. It is anticipated that any pollen release that is timed to occur in advance of the natural pollen shed of the female parents will be effective.

This invention can operate in any crop plant to either improve or enable hybrid seed production. It can operate in any environment including, but not limited to, ideal or target growing environments, off-season environments, or controlled environments (e.g. shade/glass/green/hoop houses, growth chambers, vertical farming facilities, hydroponic facilities, aeroponic facilities etc.). Pollen$^M$ can be applied as soon as females are viable and irrespective of pollen$^F$ or other undesired pollen viability, as long as all current viable females are cross pollinated during a period when pollen$^F$ or other pollen from undesirable sources is not actively shedding. This invention can also be used to improve current seed production practices even when all conventional components are present, thus improving hybrid seed purity levels in challenging production situations even though male sterility and/or isolation and/or male plants are employed. This invention could apply in parent increase fields—fields in which inbred seeds of a specific genotype are planted and allowed to self-pollinate. The resulting seed set from this self-pollination results in much larger quantities of inbred seeds, which will be used as a parent source for making hybrids at a later date. Using the invention in parent increase fields of sterile female parents avoids the need for isolation or maintainer lines (similar to cytoplasmic male sterile lines, but having viable pollen and producing normal seed) to be present. Likewise, the invention can be applied in normal parent production fields to improve the purity of the resulting seed. This invention could also apply in research settings to eliminate the need for daily shoot bagging to avoid cross contamination or to avoid de-tasseling in isolated crossing blocks (for creating experimental hybrid seed in small quantities).

In cases where very high purity levels are required, or in cases when purity is not expected to be as high as desired, further steps can be taken to purify hybrid seed lots to any desired level from self and cross contaminated seed that is in a seed mixture that has been harvested from any hybrid production block, including conventional hybrid systems in any crop. Similarly, since the invention described herein can be executed at varying levels of proficiency, further steps can be used to purify the seed lots to any desired level of purity. For example, employing a genetic marker in the male parent line that is transmitted in pollen$^M$ and expressed in the resulting seed as a distinct and distinguishable phenotype would allow for further purification of the seed lot by sorting. Examples of such a method are disclosed in International Publication WO 2014/147005. Moreover, techniques of this nature are typically used in the white seed corn industry, in which white and yellow corn can be easily sorted with automated seed sorters. The genetic marker may confer a phenotype that is distinguishable on the basis of seed color, seed color intensity or pattern, seed shape, seed size, seed density, or other seed characteristics. A seed company could employ their own specific marker as distinct from other companies, such as distinct native seed traits or genetically modified color markers that would potentially be invisible to the naked eye. The seeds may then be visually or mechanically sorted based on the marker phenotype. See, for example, Raboy et al. (2000) *Plant Physiol.* 124: 355-368; Evans, M. M. S. & Kermicle, J. L. (2001) *Genetics* 159: 303-315; Jenkins, M. T. (1925)*J. Heredity* 16: 307-310; and Chase, S. (1949) *Genetics* 34: 328-332). For some crops in developing nations where labor is very inexpensive, this could be done manually, while in other situations it would be more economical to have an automated or semi-automated seed sorter such as a Satake Seed Sorter, for example, or an optical scanning system capable of scanning and sorting the seeds In maize, for example, the native trait purple plumule (PP) (Chase (1949) Genetics 34: 328-332) may be used as the male phenotypic marker that is bred into all male inbreds and is inherited via pollen$^M$, with an automated seed sorter as the method of sorting. The invention may proceed as described above, but with the male including a marker that could be used to measure the resulting level of hybrid purity. After harvest, a quick assay of a sub-sample of seed could determine if the PP seed is at high enough purity to avoid a seed sort to increase purity. If it is not at the prescribed level, seed would be run through an automated seed sorter, for example, to separate PP seed, which represents hybrid seed, from colorless embryo seed, which represents self and cross pollinated contamination seed. This may be done in line with normal conditioning processes in a seed production plant. Moreover, the non-hybrid, colorless embryo seed could be sold as grain or discarded.

Examples of markers that can be used in maize include, but are not limited to, white/yellow endosperm, yellow/orange endosperm, opaque/normal endosperm, normal/purple plumule, colorless/purple aleurone, starch endosperm mutants, or any combination of these markers and other maize markers. In soybean, markers that can be used include, but are not limited to, green and yellow cotyledons. Non-crop specific transgenic markers include, but are not limited to, color marker genes (such as DsRed2) or any transgene that alters any normal seed phenotype, such as transgenes that increase anthocyanin or other pigments in a seed part or transgenes that alter the color of cotyledons. Further examples of such markers can be found in International Publication WO 2014/147005.

The added use of the sorting step using a marker is most appropriate and economical when hybrid purity results are achieved that are significantly better than would be obtained via conventional methods without male sterility and/or with less than standard isolation, but do not reach purity levels high enough for commercial sale. For example, it is estimated, based on the inventor's data, that the contamination (from mostly female self-pollination) in a hybrid seed lot for maize production without the usual use of male sterility or isolation would be greater than 70%, whereas contamination levels for a seed lot grown using the techniques of the present invention, also without male sterility or isolation, would cut the contamination in half or more, to 35% contamination or less. While contamination of 35% is not as low as would be required for some crops, like corn, for current non-hybrid crops like soybean, this could be adequate to begin producing the crop as a hybrid. For example, in one prior method involving soybean, about 70% purity was attained in hand crosses for developing breeding crosses. In corn, there is also field-based evidence for decreased contamination by adventitious pollen at higher yield levels (Astini, J. P. et al (2009) *Agronomy J.* 101: 373-380). Typically, the non-hybrid seed that is sorted out during any sorting step is sold as grain. By using the invention disclosed herein, it would be possible to sort out the non-hybrid seed into two categories—one for grain (outcrossings and other non-self contaminants) and a second portion (selfs) that could be sold as a self-pollinated variety, providing a value-added by-product of the sorting process.

As will be appreciated by one of skill in the art, an added benefit resulting from the practice of this invention is increased seed yield. The deliberate and intentional application of pollen to the fertile female parent plant will result in increased pollination events in comparison to naturally occurring pollinations. Depending upon the pollen$^M$ selected for use in practicing the invention, pollination rates may be considerably increased and as a result, yield will also be significantly higher than would otherwise be achieved. On average, the inventors expect a yield increase of at least 15% as a result of the practice of the invention. Depending upon the condition of the female parent plants, the choice of pollen used, environmental conditions and other factors, yield increases of significantly more than 10% are expected, including yield increases of more than 100% in some circumstances, compared to the expected yield without practicing the method of the invention.

The following examples illustrate the present invention in more detail and are illustrative of how the invention described herein could be implemented in corn. The basic method could apply to any crop with crop specific modifications as appropriate. Examples 1 to 4 occurred in fields in central Iowa during the summer of 2015.

Example 1

The invention described herein was practiced using a sweetcorn hybrid that was homozygous recessive for a gene causing a shriveled kernel phenotype at maturity (the shrunken or sugary locus (Jennings, P. H. and C. L. McCombs, (1969) Phytochemistry 8(8):1357-1363) and homozygous recessive for the yellow loci which results in white endosperm (Buckner, B. et al. (1990) The Plant Cell, Vol 2, 867-876). This sweetcorn hybrid was used as the female and was cultivated in two 36.5 meter (120 foot) rows with no isolation from normal commodity grain corn plants (yellow endosperm kernels) and was not rendered male sterile (i.e. not de-tasseled). Males that had the white and not shriveled endosperm characteristic were present in ten 4.5 meter (15 foot) rows that were cultivated, on average, 6 meters (20 feet) from the female sweetcorn rows. The invention was practiced by coercing pollen from the tassels of the white endosperm males (pollen$^M$) in the earliest part of the natural pollen shed period at approximately 8:30 am. The pollen was collected by bagging the tassels and collecting the pollen in the bags. The pollen$^M$ was then immediately directed to the sweetcorn female silks by hand using techniques well known in the art involving gentle tapping on the bag of pollen to release the pollen grains onto the silks. Using this method, shriveled kernels represent self-pollinated contaminating kernels, yellow kernels represent outcross contaminants, and white kernels represent the intended F1 cross. A total of 30,821 kernels were generated using this method. Several sweetcorn females did not have pollen$^M$ directed towards them and were allowed to open pollinate. A total of 28,896 kernels were generated from these open pollinated ears, and they were used as a control.

Table 2 shows that there was a decrease in total contaminants from both self- and cross-contamination of 18%. This was a lower decrease in contamination than was expected, but still represents a substantial improvement in purity levels. Upon reflection, analysis, and closer examination of this example, it became apparent that there were several factors that limited the system from achieving even lower contamination. The sweetcorn used in this example was used for convenience because it provided an easy marker to identify contaminants, but had very large tassels, with 5-10× or more pollen than an average female parent of a hybrid. The effect of this large amount of pollen can be easily seen by the high percentage of self-pollinations in the open pollinated ears that served as controls, which was 93% in this example and 96% in example 2 below. For normal grain corn females, this number would be expected to be in the 50-80% range with similar cultivation practices. In example 4 below, using a white grain female, the selfing percent was only 78%. Another factor affecting the outcome of this example is that we did not attempt to fully implement the invention by pollinating well before the females started shedding pollen. We simply attempted to apply the invention by making the directed pollinations at the very beginning of natural pollen shed to attempt to out-compete the contaminants. This approach was intended to simply show the potential of the invention using only a partial implementation. Finally, another factor that limited the decrease in contaminants was that the pollen from the white corn was from inbreds, and has been shown to be less competitive in comparison to hybrid pollen (i.e. the sweetcorn pollen). In light of these factors, a decrease of 18% contaminants is a reasonable improvement in purity levels.

TABLE 2

Decrease in contamination from self-pollinations and outcross contaminations of the white sweetcorn female parent when using white males with the invention described herein

| Pollination type | Open-pollinated Control* | | On-demand invention White on White | |
|---|---|---|---|---|
| | # of kernels | % of total | Sweetcorn # of kernels | % of total |
| Intended F1 cross (white) | 539 | 2% | 7242 | 23% |
| Self-pollinated contaminants (shriveled) | 26798 | 93% | 22730 | 74% |
| Outcross contaminants (yellow) | 1532 | 5% | 849 | 3% |
| Total: | 28869 | N/A | 30821 | N/A |
| On-demand decrease in contamination | | 18% | | |

Example 2

In another working example, the invention described herein was practiced using a sweetcorn hybrid that was homozygous recessive for a gene causing a shriveled kernel phenotype at maturity (the shrunken or sugary locus) and homozygous recessive for the yellow loci which results in white endosperm. This sweetcorn hybrid was used as the female and was cultivated in two 69 meter (225 foot) rows with no isolation from normal commodity grain corn plants (yellow endosperm) and was not rendered male sterile (i.e. not de-tasseled). The surrounding normal commodity grain corn plants were used as males and had a normal endosperm (not shriveled) characteristic, and were present in all adjacent rows to the females. Further, water was sprayed on the tassels of the female rows at about 8:15 am in the morning to delay pollen shed from these female rows until about 8:45 am. After spraying the water on the female tassels, the invention was immediately practiced by coercing pollen$^M$ from the tassels of the yellow endosperm males by bagging the tassels and collecting the pollen in the bags. The pollen$^M$ was then immediately directed to the sweetcorn female silks by hand using techniques well known in the art involving gentle tapping on the bag of pollen to release the pollen grains onto the silks. This step was conducted prior to these females shedding any pollen. Using this method, shriveled kernels represent self-pollinated contaminant kernels and yellow kernels represent the intended F1 cross. There is no measure of out-cross contamination. A total of 34473 kernels were generated using this method. Several sweetcorn females did not have pollen$^M$ directed towards them and were allowed to open pollinate. A total of 4914 kernels were generated from these open pollinated ears, and they were used as a control.

Table 3 shows that there was a decrease in total contaminants from both self- and cross-contamination of 31%. This decrease in contamination is substantial, particularly given the difficult prototype that this example represents, in that the tassels and pollen shed from the designated female plants is immense (5-10× or more than a normal female hybrid parent). These results reflect implementation of the invention as described herein, but even higher rigor could be applied to improve the results further. If a source of preserved pollen was used, the pollinations could have been conducted at an earlier time in the morning to give the intended pollen more time to grow down the silks and fertilize the eggs of the female.

TABLE 3

Decrease in contamination from self-pollinations of the white sweetcorn female parent when using yellow males with the invention described herein.

| | | | On-demand invention | |
|---|---|---|---|---|
| | Open-pollinated | | Yellow on White | |
| Pollination type | Control* | % of total # of kernels | Sweetcorn | % of total |
| Intended F1 cross (yellow) | 192 | 4% | 12837 | 37% |
| Self-pollinated contaminants (shriveled) | 4722 | 96% | 21636 | 63% |
| Outcross contaminants (no diagnostic) | 0 | 0% | 0 | 0% |
| Total: | 4914 | N/A | 34473 | N/A |
| On-demand decrease in contamination | | 31% | | |

Example 3

In this example, the invention was simulated using a homozygous waxy female parent and a mix of male parents that contained the functional or wild-type allele at the waxy locus (Nelson, O. E. (1968) Genetics 60: 507-524). The waxy allele is recessive and when it is in the homozygous state, representing self-pollination contaminants, it gives a characteristic opaque phenotype to the kernels which is easily recognizable to the naked eye. The females were cultivated in three 4.6 meter (15 foot) rows with no isolation and they were not rendered male sterile (i.e. not de-tasseled). Males were present in proximity and adjacent on all sides of the female rows. The invention was practiced by bagging the male plant tassels and coercing pollen$^M$ from males in the earliest part of the natural pollen shed period at approximately 8:30 am, thereby collecting it in the bags. The pollen$^M$ was then immediately directed to the waxy female silks by hand using techniques well known in the art involving gentle tapping on the bag of pollen to release the pollen grains onto the silks. There were 14 ears derived in this example for a total of 3217 kernels. Table 4 shows the results for this example. While a control was not included directly in this experiment, a-priori expectations from the literature are that there would be a minimum of 50% contamination from self-pollinations of the female without using the invention (See, for example, Paterniani E. & Stort, A. C. (1974) *Euphytica* 23: 129-134; Ma, B. L. et al. (2004) *Crop Sci.* 44: 1273-1282). Using the control from Example 4 below, one would expect contamination levels of about 78% without using the invention. In this example, self-pollination contamination was reduced to 2%. This represents a reduction of 97% in the contamination level from self-pollination. In this example, hybrid seed would have been made that meets the standard 95% purity level.

TABLE 4

Decrease in contamination from self-pollinations of the waxy female parent when using wild-type males with the invention described herein.

| | | | On-demand invention | |
|---|---|---|---|---|
| | Open-pollinated | | wild-type | |
| Pollination type | Control* | % of total # of kernels | on waxy | % of total |
| Intended F1 cross (vitreous) | 1337 | 22% | 3217 | 98% |
| Self-pollinated contaminants (waxy) | 4724 | 78% | 66 | 2% |
| Outcross contaminants (no diagnostic) | ND | ND | ND | ND |
| Total: | 6061 | N/A | 3283 | N/A |
| On-demand decrease in contamination | | 97% | | |

*Used the yellow/white control for the waxy control. Controlled self-pollinated waxy plants in the same rows were 100% waxy.

Example 4

The invention described herein was further simulated using a homozygous white endosperm female (i.e. homozygous recessive at the yellow loci (y/y)) parent and a mix of male parents that were yellow endosperm. The females were cultivated in a field in Iowa in the summer of 2015 in one 4.6 meter (15 foot) row with no isolation and the plants were not rendered male sterile (i.e. not de-tasseled). Males were present in proximity and adjacent on all sides of the female rows. The invention was practiced by bagging the male tassels and coercing pollen$^M$ from males in the earliest part of the natural pollen shed period at approximately 8:30 am. The pollen$^M$ was then immediately directed to the waxy female silks by hand using techniques well known in the art involving gentle tapping on the bag of pollen to release the pollen grains onto the silks. There were 5 ears derived in this example for a total of 888 kernels. There were several plants within this row and in other nearby rows with white endosperm females that were allowed to open pollinate and were used as controls, constituting a total of 6061 kernels. Table 5 shows that there was a 79% reduction in contamination in this example. This example would be a case where one could utilize the endosperm color marker to improve purity by sorting out the white endosperm kernels (i.e. the self-pollinations) to bring purity up to the standard 95% level.

TABLE 5

Decrease in contamination from self-pollinations of the white endosperm female parent when using yellow endosperm males with the invention described herein.

| | | | On-demand invention | |
|---|---|---|---|---|
| | Open-pollinated | | Yellow on white | % of |
| Pollination type | Control* | % of total # of kernels | | total |
| Intended F1 cross (yellow) | 1337 | 22% | 744 | 84% |
| Self-pollinated contaminants (white) | 4724 | 78% | 144 | 16% |

TABLE 5-continued

Decrease in contamination from self-pollinations of
the white endosperm female parent when using yellow
endosperm males with the invention described herein.

| Pollination type | Open-pollinated Control* | % of total # of kernels | On-demand invention Yellow on white | % of total |
|---|---|---|---|---|
| Outcross contaminants (no diagnostic) | ND | ND | ND | ND |
| Total kernels | 6061 | N/A | 888 | N/A |
| On-demand decrease in contamination | | 79% | | |

Example 5

A corn seed hybrid production block is planted in exactly the manner as is currently practiced, except that isolation distances are reduced by 50% or more, de-tasseling of the female parents is practiced at a reduced level so as to allow 10% of the females to have shedding tassels (rather than the standard 1% shedding tassels), and the percent of male plants is reduced by 50% or more. Male parent pollen is collected and preserved and is obtained from a storage facility and applied to the female parent silks at 6 am.

Anticipated results are that contamination would be reduced by 50% or more when compared to the same production practices without implementing the invention. The parameters in this example might be aptly applied for hybrid seed production blocks that utilize a male that sheds an average to slightly more than average amount of pollen, and a female that sheds an average amount of pollen.

Example 6

A corn seed hybrid production block is planted in exactly the same manner as is currently practiced, including the standard isolation distance and standard de-tasseling practices (to enable 1% or less of the females to have a shedding tassel) and to include the male at the standard percentage based on the amount of pollen that the male sheds. For example, assume the male is determined to be a "poor" male and sheds less than 2 million grains of pollen per tassel. In this case, some seed company standards would deem this male as sub-standard and would discard it, regardless of how high yielding the hybrids that it makes may be. Other seed companies might take a risk with this male and plant it at a high ratio relative to the female in the hybrid seed production block.

In this example, the male is planted in a 2:4 ratio (2 male rows for every 4 female rows) with a border of 10 rows of male around the entire production block. The invention is practiced using male parent pollen that has been collected and preserved and is obtained from a storage facility and precisely applied to the female parent silks at 6 am.

Anticipated results are that contamination would be reduced to levels that meet standards for certification and sale of hybrid seed. Under normal production conditions, production fields as described in this example may average 5% contamination due to the poor male that is being utilized. The range around this average may be from 1-8% contamination, depending on the environmental conditions for any given field (e.g. wind and proximity of a neighboring corn field). This implies that half of the production fields with this scenario would produce sub-standard (<95% purity) hybrid seed that would potentially need to be discarded. For fields in which the invention has been implemented, using a decrease in contamination by 50% implies that average contamination would now be 2.5%, with a potential range from 0% to 5%. In this case, with a normal distribution, one would expect 90-100% of the production fields in this example to produce seed that meets the 95% standard.

Example 7

A corn parent seed production field is an isolated field (201 meters (660 feet) or more) that contains only one parent of a given hybrid. The parent is allowed to open-pollinate, or essentially self-pollinate, to increase its seed so that there is sufficient parent seed to use the parent in hybrid seed production. Several generations of parent seed increases are necessary to produce enough parent seed to eventually use the parent in a hybrid seed production block.

In this parent seed production example, there would be no isolation from other potential contaminating corn. The invention is practiced using the parent's pollen that has been collected and preserved and is obtained from a storage facility and applied to the parent's silks at 6 am. Anticipated results are that contamination would be reduced by 50% or more when compared to the same production practices without implementing the invention. The parameters in this example might be applied when isolation distances are impossible to attain and yet a parent needs to be increased to make hybrid seed for an important product. This scenario can be encountered in contra season growing locations (e.g. Hawaii) when a seed company is trying to increase a parent for the coming growing season.

Summary of Working Examples. Examples 1-4 illustrate how this invention can work to varying levels of success depending upon the male characteristics of the designated male and female. In all four of these examples, while a decrease in contamination was observed using a simulation of the invention or using the invention itself, it would have been ideal to utilize preserved pollen that was available on-demand to illustrate the utility and potential of this invention. This would have allowed for the application of the pollen to the silks at a more ideal time which it could avoid all competition with the natural pollen cloud and would have such a large head start growing down the target silk, such that the probability of other contaminating pollen fertilizing the female would be greatly reduced, thus decreasing the percent contamination to an even lower level than these examples.

Although various representative embodiments of this invention have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The invention claimed is:

1. A method of maize seed production, said method comprising:
  a. growing a designated female maize parent plant, said designated female parent plant comprising both male and female components; having a pollination window and wherein said designated female parent plant is exposed to undesirable pollen from an undesirable pollen source during said pollination window; and said pollination window has a first daily period wherein undesirable pollen is not shed and a second daily period wherein undesirable pollen is shed;
  b. intentionally pollinating said designated female parent plant on one or more occasions with designated maize male pollen during said daily first period wherein pollen is not shed from said undesirable pollen source, when said male components of said designated female parent plant are not releasing viable pollen and when plants of the same species in proximity to said designated female parent plant are not releasing pollen;
  c. growing the designated female plant to maturity; and
  d. harvesting the seed produced by said designated female plant; wherein the designated male pollen is from a maize plant genetically different from the designated female parent plant; and wherein the designated female parent plant is not covered to prevent pollination from the undesirable pollen.

2. The method of claim 1 wherein the designated male pollen is comprised of one or more of the following:
  a. Fresh pollen
  b. Preserved pollen.

3. The method of claim 1 wherein the intentional pollination is conducted by any one or more of: mechanical means, pneumatic means, positive pressure, negative pressure, manual means, or combinations thereof.

4. The method of claim 1 wherein the intentional pollination is conducted by automated or semi-automated means.

5. The method of claim 4 wherein the automated or semi-automated means is a vehicle or drone.

6. The method of claim 1 wherein said designated male pollen is fresh pollen which has been harvested from one or more of a field, a growth chamber, a greenhouse, a glasshouse, a shade house, a hoop house, a vertical farming facility or a hydroponic facility.

7. The method of claim 1 wherein said designated male pollen is preserved pollen which has been previously collected and preserved by cooling, chilling, cryopreservation, freezing, freeze drying, or storage in liquid nitrogen.

8. The method of claim 1 wherein the designated male pollen has been collected from one or more of:
  i. a source with altered circadian rhythm; and
  ii. a source with normal circadian flowering, but wherein said male components of said designated female parent plants are delayed; and
  iii. a source with normal circadian flowering wherein said male components of said designated female parent plants are allowed to shed with no delay.

9. The method of claim 1 wherein said designated male pollen is applied on more than one occasion to the same designated female parent plant.

10. The method of claim 1 wherein said designated male pollen is applied at the time which the designated female parent plant first becomes receptive to said pollen.

11. The method of claim 1 wherein the maturity of said male components is delayed with a treatment.

12. The method of claim 1 in which said designated male pollen is obtained from a single genetic source.

13. The method of claim 1 in which said designated male pollen is obtained from multiple genetic sources and is combined prior to application.

14. A method of maize seed production comprising:
  a) growing a plurality of designated female parent maize plants, wherein said designated female parent plants includes male components and female components, said designated female parent plants receive pollen during a pollination window, wherein said pollination window includes a period wherein pollen is not shed from said male components and a period wherein pollen is shed from said male components;
  b) intentionally pollinating said plurality of designated female parent plants, on one or more occasions, with designated male plant pollen when said male components of said designated female parent plant are not releasing viable pollen and when plants of the same species in proximity to said plurality of designated female parent plants are not releasing pollen;
  c) growing the designated female plant to maturity; and
  d) harvesting the seed produced by said designated female plant;
wherein the designated female parent plant is genetically different from the designated male pollen plant; and wherein the designated female parent plant is not covered to prevent pollination from an undesirable pollen.

15. The method of claim 14 wherein said male components of said designated female parent plant cycles between a plurality of periods wherein pollen is not shed from said male components and periods wherein pollen is shed from said male components.

16. The method of claim 15 wherein one period wherein pollen is not shed from said male components and one period wherein pollen is shed from said male components total a 24-hour day.

17. The method of claim 16 wherein said intentional pollination occurs on a plurality of days during a plurality of said periods wherein pollen is not shed from said male components.

18. The method of claim 14 wherein said intentional pollination occurs after silk emergence of the designated female parent plants but before pollen shed of said designated female parent plants male components.

19. The method of claim 14 wherein said intentional pollination occurs after both silk emergence and pollen shed of the designated female parent plant but at a time when pollen shed is not actively occurring.

20. The method of claim 1 wherein said undesirable pollen source is selected from the group consisting of self-pollen, sib-pollen, undesirable pollen having a different genetic background from said designated female parent plant, and combinations thereof.

21. The method of claim 1 wherein the step of intentionally pollinating said designated female parent plants with designated male pollen occurs in the morning before said designated female parent plant is exposed to said undesirable male pollen.

22. The method of claim 1 further comprising planting a seed production field having a plurality of designated female parent plants and a plurality of designated male parent plants, wherein said designated male parent plants produce designated male pollen that naturally pollinates at least a portion of said designated female parent plants and wherein said intentional pollination step results in intentional pollination of at least a portion of said designated female parent plants.

23. The method of claim 22 wherein said seed comprises at least 95% of an intended hybrid cross.

24. The method of claim 22 wherein designated male pollen is collected from said designated male parent plants in said seed production field for the intentional pollination step.

25. The method of claim 24 wherein said seed comprises at least 95% of an intended hybrid cross.

26. The method of claim 22 wherein designated male pollen is collected from designated male parent plants in said seed production field prior to emergence of silks on said designated female parent plant.

27. A method of maize seed production, said method comprising intentionally delivering desired pollen at least once to a designated female parent plant during a daily window of time when said female is receptive to pollen, said daily window of time being prior to the designated female parent's pollen becoming viable, growing the designated female plant to maturity, and harvesting the seed produced by said designated female plant; wherein the desired pollen is from a maize plant that is genetically different from the designated female parent plant; and wherein the method includes the reduction or elimination of the need of one or more of the following conditions:
  i) male sterility of the designated female plant;
  ii) physical and/or temporal isolation of said designated female plant from undesirable pollen of the same species; and
  iii) male pollinator plants to be grown in proximity of said designated female plant.

28. A method of maize seed production, said method comprising growing a designated female parent plant, said designated female parent plant having a window of time during which successful cross-pollination can occur prior to production of pollen from said designated female parent plant, intentionally pollinating said designated female parent plant during said window when the female component of said designated female plant is open to receive pollen from a designated male plant and before male components of said designated female plant produce pollen on the day of said intentionally pollinating, growing the designated female plant to maturity, and harvesting the seed produced by said designated female plant; wherein the designated male plant is genetically different from the designated female parent plant; and wherein the method includes the reduction or elimination of the need of one or more of the following conditions:
  i) male sterility of the designated female plant;
  ii) physical and/or temporal isolation of said designated female plant from undesirable pollen of the same species; and
  iii) male pollinator plants to be grown in proximity of said designated female plant.

29. A method of maize seed production, said method comprising growing a designated female parent plant, delivering desired pollen to said designated female parent during a daily window of time when pollen from said designated female parent plant is not shedding, growing the designated female plant to maturity, and harvesting the seed produced by said designated female plant; wherein the desired pollen is from a maize plant that is genetically different from the designated female parent plant; and wherein the method includes the reduction or elimination of the need of one or more of the following conditions:
  i) male sterility of the designated female plant;
  ii) physical and/or temporal isolation of said designated female plant from undesirable pollen of the same species; and
  iii) male pollinator plants to be grown in proximity of said designated female plant.

30. A method of maize seed production, said method comprising the intentional application of designated male pollen to a designated female plant where the designated female plant parent is in a state when the female components of said designated female plant are ready to receive pollen but the male components of said designated female plant are not releasing pollen; wherein the designated pollen is from a maize plant that is genetically different from the designated female parent plant; and wherein the method includes the reduction or elimination of the need of one or more of the following conditions:
  i) male sterility of the designated female plant;
  ii) physical and/or temporal isolation of said designated female plant from undesirable pollen of the same species; and
  iii) male pollinator plants to be grown in proximity of said designated female plant.

31. The method of claim 1, wherein the method further includes the reduction or elimination of the need of one or more of the following conditions:
  i) male sterility of the designated female plant;
  ii) physical and/or temporal isolation of said designated female plant from undesirable pollen of the same species; and
  iii) male pollinator plants to be grown in proximity of said designated female plant.

32. The method of claim 14, wherein the method further includes the reduction or elimination of the need of one or more of the following conditions:
  i) male sterility of the designated female plant;
  ii) physical and/or temporal isolation of said designated female plant from undesirable pollen of the same species; and
  iii) male pollinator plants to be grown in proximity of said designated female plant.

* * * * *

UNITED STATES PATENT AND TRADEMARK OFFICE
CERTIFICATE OF CORRECTION

PATENT NO. : 10,905,060 B2
APPLICATION NO. : 15/192485
DATED : February 2, 2021
INVENTOR(S) : Todd Krone It is certified that error appears in the above-identified patent and that said Letters Patent is hereby corrected as shown below:

On the Title Page

Item [12] should read "Krone et al."

Item [72], Inventors, please add "Jason Cope, Ankeny, IA, (US)", "Mark E. Westgate, Ames, IA (US)", and "George Singletary, Ankeny, IA (US)"

Signed and Sealed this
Twentieth Day of August, 2024

Katherine Kelly Vidal
*Director of the United States Patent and Trademark Office*